United States Patent
Vairavan et al.

(10) Patent No.: US 12,277,929 B2
(45) Date of Patent: *Apr. 15, 2025

(54) SYSTEM AND METHOD FOR DETECTING COGNITIVE DECLINE USING SPEECH ANALYSIS

(71) Applicant: Janssen Pharmaceutica NV, Beerse (BE)

(72) Inventors: Srinivasan Vairavan, Cranbury, NJ (US); Vaibhav Narayan, Princeton, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/135,658

(22) Filed: Apr. 17, 2023

(65) Prior Publication Data

US 2024/0021192 A1     Jan. 18, 2024

Related U.S. Application Data

(63) Continuation of application No. 16/847,925, filed on Apr. 14, 2020, now Pat. No. 11,631,395.

(Continued)

(51) Int. Cl.
    *G10L 15/08*     (2006.01)
    *G06N 20/10*     (2019.01)
    *G10L 15/06*     (2013.01)

(52) U.S. Cl.
    CPC .............. *G10L 15/08* (2013.01); *G06N 20/10* (2019.01); *G10L 15/063* (2013.01); *G10L 2015/0631* (2013.01)

(58) Field of Classification Search
    CPC ................... G10L 15/08; G10L 15/063; G10L 2015/0631; G10L 17/26; G10L 25/51;

(Continued)

(56) References Cited

U.S. PATENT DOCUMENTS

| | | |
|---|---|---|
| 968,517 A | 8/1910 | Pierman |
| 8,639,639 B2 | 1/2014 | Jamil et al. |

(Continued)

FOREIGN PATENT DOCUMENTS

| | | |
|---|---|---|
| WO | WO2016028495 A1 | 2/2016 |
| WO | WO-2018048953 A1 | 3/2018 |

OTHER PUBLICATIONS

Roark et al, "Spoken Language Derived Measures for Detecting Mild Cognitive Impairment", Sep. 2011, IEEE Transactions on Audio, Speech, and Language Processing, vol. 19, No. 7, 2081-2090 (Year: 2011) (Year: 2011).*

(Continued)

*Primary Examiner* — Michael N Opsasnick
(74) *Attorney, Agent, or Firm* — Grimes & Yvon LLP

(57) ABSTRACT

System and method for detecting cognitive decline in a subject using a classification system for detecting cognitive decline in the subject based on a speech sample. The classification system is trained using speech data corresponding to audio recordings of speech from normal and cognitive decline patients to generate an ensemble classifier comprising a plurality of component classifiers and an ensemble module. Each of the plurality of component classifiers is a machine-learning classifier configured to generate a component output identifying a sample data as corresponding to a normal patient or a cognitive patient. The machine-learning classifier is generated based on a subset of available features. The ensemble module receives component outputs from all of the component classifiers and generates an ensemble output identifying the sample data as corresponding to a normal or cognitive decline patient based on the component outputs.

16 Claims, 8 Drawing Sheets

Related U.S. Application Data

(60) Provisional application No. 62/834,170, filed on Apr. 15, 2019.

(58) Field of Classification Search
CPC ........ G10L 25/75; G06N 20/10; G06N 20/00; A61B 5/4803; A61B 7/00; A61B 5/7264; A61B 5/16; A61B 5/6898; A61B 5/165; G16H 50/70; G06K 9/6234
See application file for complete search history.

(56) References Cited

U.S. PATENT DOCUMENTS

| | | | |
|---|---|---|---|
| 10,478,111 B2 | 11/2019 | Knoth et al. | |
| 11,631,395 B2* | 4/2023 | Vairavan | A61B 5/4803 704/251 |
| 2008/0208072 A1* | 8/2008 | Fadem | A61B 5/291 600/544 |
| 2009/0208913 A1 | 8/2009 | Xu et al. | |
| 2011/0055141 A1 | 3/2011 | Jamil et al. | |
| 2015/0112232 A1 | 4/2015 | Quatieri et al. | |
| 2015/0265205 A1* | 9/2015 | Rosenbek | A61B 7/00 600/586 |
| 2015/0318002 A1 | 11/2015 | Karam et al. | |
| 2016/0253999 A1 | 9/2016 | Kang et al. | |
| 2017/0177826 A1 | 6/2017 | Alexander et al. | |
| 2017/0251985 A1 | 9/2017 | Howard | |
| 2017/0258390 A1* | 9/2017 | Howard | A61B 5/369 |
| 2018/0042546 A1 | 2/2018 | Hwang et al. | |
| 2018/0214061 A1* | 8/2018 | Knoth | G10L 17/26 |
| 2018/0322894 A1 | 11/2018 | Kim et al. | |
| 2018/0322961 A1* | 11/2018 | Kim | G06N 3/08 |
| 2019/0043610 A1* | 2/2019 | Vaughan | G16H 10/60 |
| 2019/0043618 A1 | 2/2019 | Vaughan et al. | |
| 2019/0201691 A1* | 7/2019 | Poltorak | A61B 5/165 |
| 2019/0247662 A1* | 8/2019 | Poltroak | A61N 1/36053 |

OTHER PUBLICATIONS

Schaffer et al. ("Predicting with Confidence: Classifiers that Know What They Don't Know", Procedia Computer Science 114 (2017) 200-207) (Year: 2017).*

Tsang et al., "Harnessing the Power of Machine Learning in Dementia Informatics Research: Issues, Opportunities, and Challenges", IEEE Reviews in Biomedical Engineering, vol. 13, Mar. 2019, pp. 113-129.

Schaffer et al., "Predicting with Confidence: Classifiers that Know What They Don't Know", Procedia Computer Science, vol. 114, Nov. 2017, pp. 200-207.

Johann de Jong, "SVM with recursive feature elimination in R" https://johanndejong.wordQress.com/2016/01/17/svm-with-recursive-feature-elimination/ Jan. 17, 2016 (Algorithms, Bioinformatics, Machine learning, R programming), 6 sheets.

Roark et al, "Spoken Language Derived Measures for Detecting Mild Cognitive Impairment", Sep. 2011, IEEE Transactions on Audio, Speech, and Language Processing, vol. 19, No. 7, 2081-2090 (Year: 2011).

Schaeffer et al., "A Genetic Algorithm Approach for Discovering Diagnostic Patterns in Molecular Measurement Data," Proc. CIBCB, IEEE, 392-399 (2005).

* cited by examiner

SYSTEM AND METHOD FOR DETECTING COGNITIVE DECLINE USING SPEECH ANALYSIS

PRIORITY CLAIM

The present application is a continuation of U.S. application Ser. No. 16/847,925 entitled "System and Method for Predicting Cognitive Decline" filed on Apr. 14, 2020, which claims priority to U.S. Provisional Application Ser. No. 62/834,170 entitled "System and Method for Predicting Cognitive Decline" filed on Apr. 15, 2019, the entire contents of both applications of which are hereby incorporated by reference herein.

BACKGROUND OF THE INVENTION

Mild Cognitive Impairment (MCI) causes a slight but noticeable and measurable decline in cognitive abilities, including memory and thinking skills. The changes caused by MCI are not severe enough to affect daily life and a person with MCI may not meet the diagnostic guidelines for dementia. However, those with MCI have an increased risk of eventually developing Alzheimer's disease (AD) or another type of dementia. Early therapeutic interventions may provide better prospects for success.

Episodic memory is the memory of an event or "episode." It comprises anterograde (newly encountered information) or retrograde (past events) components. A decline in verbal episodic memory occurs earliest in patients with preclinical/prodromal AD and predicts disease progression. Assessment of decline in verbal episodic memory in MCI represents early cognitive changes and can be used as a screening tool for timely detection and initiation of treatment for early/preclinical AD.

BRIEF SUMMARY OF THE INVENTION

One exemplary embodiment of the present invention is directed to a method for detecting cognitive decline in a subject. The method comprises obtaining subject baseline speech data corresponding to a plurality of audio recordings of speech of the subject in response to a first set of instructions provided to the subject, and obtaining subject trial speech data corresponding to a further audio recording of speech of the subject in response to a second set of instructions provided to the subject. The method also includes steps for extracting a plurality of features from the subject baseline speech data and the subject trial speech data and generating subject test data by normalizing the subject trial speech data using the subject baseline speech data. The method further includes analyzing the subject test data using a trained ensemble classifier. The trained ensemble classifier comprises a plurality of component classifiers and an ensemble module. Each of the plurality of component classifiers is configured to generate a component output identifying the subject test data as corresponding to a normal patient or a cognitive decline patient. Each component classifier is configured to analyze a subset of features selected from the plurality of features. The ensemble module is configured to receive the component outputs from the component classifiers and generate an ensemble output identifying the subject test data as corresponding to the normal patient or the cognitive decline patient based on the component outputs. The plurality of component classifiers is trained using training baseline speech data corresponding to prior audio recordings of speech of a group of normal and cognitive decline patients in response to the first set of instructions, and training trial speech data corresponds to prior audio recordings of speech of the group normal and cognitive decline patients in response to the second set of instructions.

A device for detecting cognitive decline in a subject is provided. The device comprises an audio output arrangement configured to generate an audio output, an audio input arrangement configured to receive audio signals and to generate data corresponding to recordings of the audio signals, and a display. The device also comprises a processor and a non-transitory computer readable storage medium including a set of instructions executable by the processor. The set of instructions operable to: direct the audio output arrangement to audibly provide a first set of instructions to a subject a plurality of times, receive, from the audio input arrangement, subject baseline speech data corresponding to a plurality of audio recordings of speech of the subject in response to the first set of instructions, direct the audio output arrangement to audibly provide a second set of instructions to the subject, receive, from the audio input arrangement, subject trial speech data corresponding to a further audio recording of speech of the subject in response to a second set of instructions, extract a plurality of features from the subject baseline speech data and the subject trial speech data, generate subject test data by normalizing the subject trial speech data using the subject baseline speech data, analyze the subject test data using a trained ensemble classifier to generate an output indicating whether the subject likely suffers from cognitive decline, and direct the display to provide a visual representation of the output to the user. The device further comprises a memory configured to store the trained ensemble classifier. The trained ensemble classifier comprising a plurality of component classifiers and an ensemble module. Each of the plurality of component classifiers configured to generate a component output identifying the subject test data as corresponding to a normal patient or a cognitive decline patient. Each component classifier configured to analyze a subset of features selected from the plurality of features. The ensemble module is configured to receive the component outputs from the component classifiers and generate an ensemble output identifying the subject test data as corresponding to the normal patient or the cognitive decline patient based on the component outputs. The plurality of component classifiers is trained using training baseline speech data corresponding to prior audio recordings of speech of a group of normal and cognitive decline patients in response to the first set of instructions, and training trial speech data corresponds to prior audio recordings of speech of the group normal and cognitive decline patients in response to the second set of instructions.

In another exemplary embodiment, a computer-implemented method for training a classification system is provided. The classification system is configured to detect cognitive decline in a subject based on a speech sample of the subject. The method comprises obtaining training baseline speech data and training trial speech data from a group of normal and cognitive decline patients. The training baseline speech data corresponds to audio recordings of speech of the group of normal and cognitive decline patients in response to a first set of instructions and the training trial speech data corresponds to audio recordings of speech of the group of normal and cognitive decline patients in response to a second set of instructions. The method also comprises extracting a plurality of features from (i) the training baseline speech data, and (ii) the training trial speech data. The method further comprises generating an ensemble classifier comprising a plurality of component classifiers and an ensemble module. Each of the plurality of component classifiers is configured to generate a component output identifying a sample data as corresponding to a normal patient or a cognitive decline patient. Each component classifier is configured to analyze a subset of features selected from the plurality of features. The ensemble module is configured to receive the component outputs from the component classifiers and generate an ensemble output identifying the sample data as corresponding to the normal patient or the cognitive decline patient based on the component outputs. The method further comprises generating a training data set by normalizing the training trial speech data using the training baseline speech data and training the ensemble classifier using the training data set.

A system for training a classification system is also provided. The classification system is configured to detect cognitive decline in a subject based on a speech sample of the subject. The system comprises a database configured to store training baseline speech data and training trial speech data from a group of normal and cognitive decline patients. The training baseline speech data corresponds to audio recordings of speech of the group of normal and cognitive decline patients in response to a first set of instructions and the training trial speech data corresponds to audio recordings of speech of the group of normal and cognitive decline patients in response to a second set of instructions. The system further comprises a computing device operably connected to communicate with the database. The computing device comprising a processor and a non-transitory computer readable storage medium including a set of instructions executable by the processor. The set of instructions operable to retrieve the training baseline speech data and the training trial speech data from the database, extract a plurality of features from (i) the training baseline speech data, and (ii) the training trial speech data, generate an ensemble classifier comprising a plurality of component classifiers and an ensemble module. Each of the plurality of component classifiers is configured to generate a component output identifying a sample data as corresponding to a normal patient or a cognitive decline patient. Each component classifier is configured to analyze a subset of features selected from the plurality of features. The ensemble module is configured to receive the component outputs from the component classifiers and generate an ensemble output identifying the sample data as corresponding to the normal patient or the cognitive decline patient based on the component outputs. The set of instructions is further operable to generate a training data set by normalizing the training trial speech data using the training baseline speech data and train the ensemble classifier using the training data set. The system further comprises a memory configured to store the trained ensemble classifier.

These and other aspects of the invention will become apparent to those skilled in the art after a reading of the following detailed description of the invention, including the figures and appended claims.

DETAILED DESCRIPTION OF THE INVENTION

The present application relates to devices and methods for detecting and/or predicting cognitive decline, in particular, MCI, by analyzing data corresponding to a speech sample of a subject or patient obtained from a neuropsychological test, such as a word list recall (WLR) test using a computer-implemented method. The neuropsychological test is capable of screening cognitive abilities of the subject, including, for example, memory. Additionally, the present application includes systems and methods for training a classification system configured to detect cognitive decline (e.g., MCI) and/or predict onset of cognitive decline or dementia (e.g., AD), based on the WLR speech sample of a subject.

Figure 1:
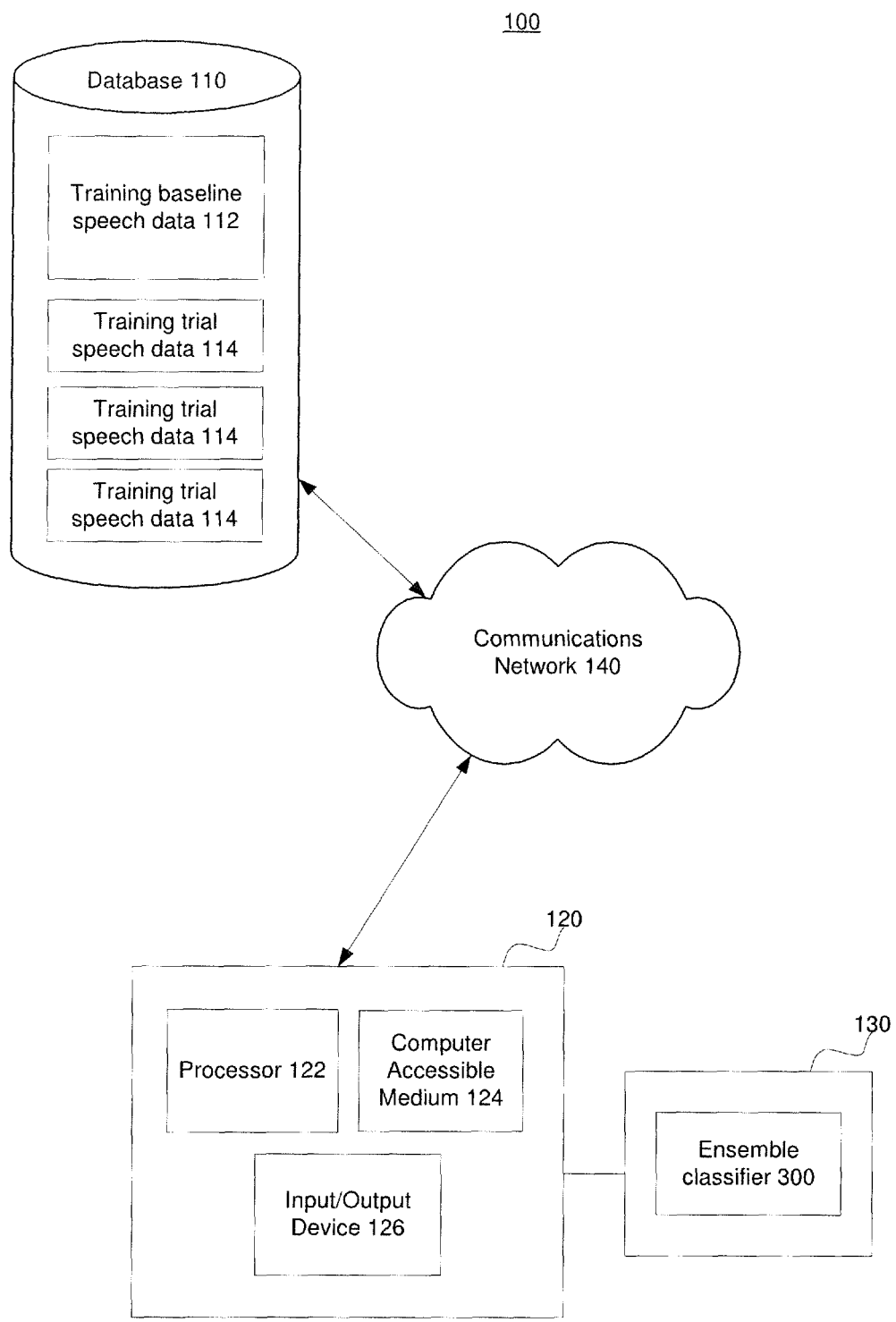
FIG. 1 shows a system for training a classification system for detecting cognitive decline based on a speech sample of a subject, according to an exemplary embodiment of the present application.

FIG. 1 shows an exemplary embodiment of a system 100 for training a classification system for detecting and/or predicting cognitive decline, in particular, MCI, based on a speech sample of a subject. The system 100 comprises a database 110 for storing various types of data, including data corresponding to audio recordings of previously administered WLR tests. Specifically, the database 110 includes training baseline speech data 112, and one or more sets of training trial speech data 114 each obtained under different experimental conditions, as will be explained further below. The database 110 may be stored on one or more non-transitory computer-readable storage media.

The database 110 may be operably connected to a computing device 120 for providing a portion of or all of the data stored within the database 110 to the computing device 120, or for allowing the computing device 120 to retrieve a portion of or all of the data stored within the database 110. As shown in FIG. 1, the database 110 is connected via a communications network 140 (e.g., Internet, Wide Area Network, Local Area Network, Cellular network, etc.) to the computing device 120. However, it is also contemplated that the database 110 can be connected directly via a wired connection to the computing device 120. The computing device 120 in this embodiment comprises a processor 122, a computer accessible medium 124, and an input/output device 126 for receiving and/or transmitting data and/or instructions to and/or from the computing device 120. The processor 122 can include, e.g., one or more microprocessors, and use instructions stored on the computer-accessible medium 124 (e.g., memory storage device). The computer-accessible medium 124 may, for example, be a non-transitory computer-accessible medium containing executable instructions therein. The system 100 may further include a memory storage device 130 provided separately from the computer accessible medium 124 for storing an ensemble classifier 300 generated and trained by the system 100. The memory storage device 130 may be part of the computing device 120 or may be external to and operably connected to the computing device 120. The memory storage device 130 may also be connected to a separate computing device (not shown) for detecting and/or predicting cognitive decline in a subject. In another embodiment, the ensemble classifier 300 may be store on another memory storage device (not shown) connected to a separate computing device (not shown) for detecting and/or predicting cognitive decline in a subject.

Figure 2:
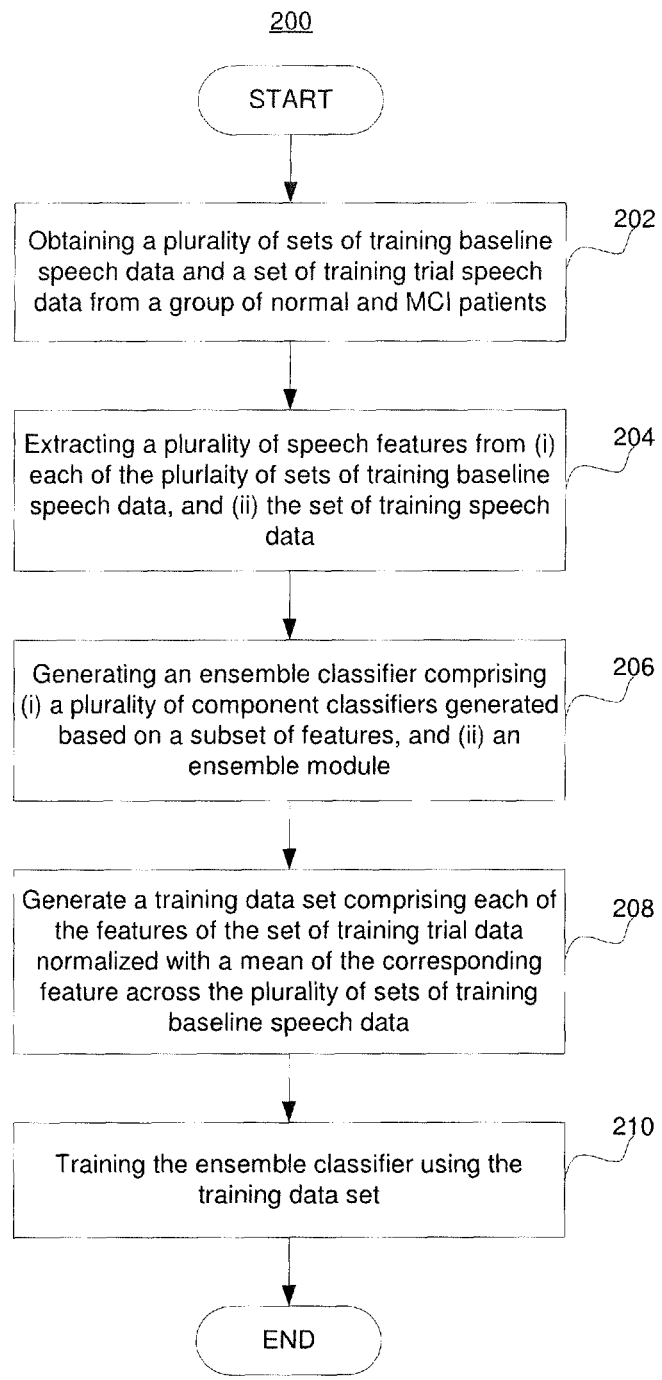
FIG. 2 shows a method for training a classification system for detecting cognitive decline based on a speech sample of a subject, according to an exemplary embodiment of the present application.

FIG. 2 shows an exemplary embodiment of a method 200 for training a classification system for detecting and/or predicting cognitive decline in a subject based on a speech sample of the subject. In particular, the method 200 generates and trains an ensemble classifier 300 for analyzing a speech sample (e.g., a WLR speech sample) to determine whether the sample correlates more to that of a normal or a cognitive decline patient (e.g., a MCI patient). The WLR speech sample may be acquired from the database 110, which may store data corresponding to previously recorded audio files from various WLR tests, such as, for example, experiments using a RAVLT for evaluating verbal episodic memory. The RAVLT is a word list based, examiner administered tool that can be used to measure verbal episodic memory. It can be used to detect and/or generate scores regarding verbal memory including rate of learning, short-term and delayed verbal memory, recall performance after interference stimulus, recognition memory, and learning pattern (serial position effect) that correlate with cognitive abilities.

In step 202, the computing device 110 receives from the database 110 a plurality of sets of training baseline speech data 112 corresponding to a plurality of sets of prior audio recordings of speech of a group of normal and cognitive decline patients. Each set of the training baseline speech data 112 corresponds to speech of the group of normal and cognitive decline patients in response to a same set of instructions for listening to a word list and recalling and speaking the same word list. For example, the training baseline speech data 112 corresponds to speech of the group of normal and cognitive decline patients in response to a first set of instructions for listening to a first word list, and immediately recalling and speaking the first word list. In one particular embodiment, the training baseline speech data 112 may comprise data corresponding to audio recordings of speech of the group of normal and cognitive decline patients from learning trials of a WLR test, such as, for example, the RAVLT test. Step 202 may utilize any suitable number of sets of the training baseline speech data 112 for establishing average baseline characteristics against which the training trial speech data 114 may be compared to identify and/or enhance the feature discriminatory signals contained within the training trial speech data 114. In particular, the training baseline speech data 112 may include learning phase data from any suitable WLR test. The training baseline speech data 112, in particular, the learning phase data, serve as baseline characteristics against which the training trial speech data 114 may be compared to generate quantitative representations of cognitive loads of the group of normal and cognitive decline patients. In some embodiments, at least 3 sets, at least 5 sets, or at least 10 sets of the training baseline speech data 112 may be used. In one exemplary embodiment, 5 sets of the training baseline speech data 112 is used.

The computing device 110 also receives from the database 110 a set of training trial speech data 114. The set of training trial speech data 114 is used by the method 200—to generate a training data set 330 for training the ensemble classifier 300 and/or to generate the ensemble classifier 300—as will be discussed further below. The training trial speech data 114 corresponds to prior audio recordings of speech of the group of normal and cognitive decline patients in response to at least one different set of instructions for recalling and speaking as compared to the training baseline speech data 112. For example, the different set of instructions may direct the patients to listen to a different word list, and immediately recall and speak the different word list. As another example, the different set of instructions may direct the patients to listen to the same word list as used for the training baseline speech data 112, but recall and speak the word list after a distraction task and/or after a delay for a period of time (e.g., at least or at about 10 minutes, at least or at about 20 minutes, or at least or at about 30 minutes). In one particular embodiment, the training trial speech data 112 may comprise data corresponding to audio recordings of speech of the group of normal and cognitive decline patients from distraction trial, post-distraction trial and/or time-delayed trial of a WLR test, such as, for example, the RAVLT test.

Figure 8:
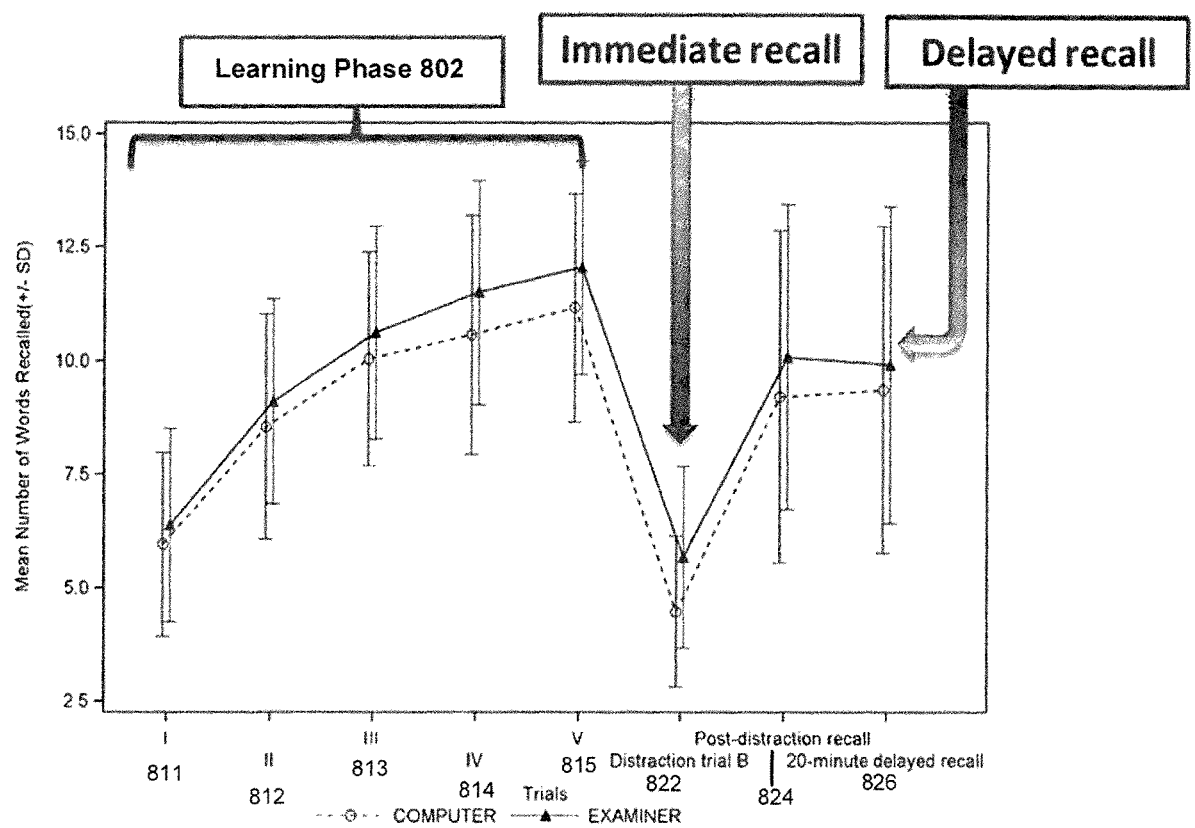
FIG. 8 shows data corresponding to mean number of words recalled across different steps in an exemplary embodiment of a Rey Auditory Verbal Learning Test (RAVLT) test, according to Example I of the present application.

In one particular embodiment, the method 200 for training a classification system for detecting and/or predicting cognitive decline in a subject based on a speech sample of the subject may utilize clinical trial data that were obtained as part of a RAVLT test from normal and MCI patients. Data corresponding to mean number of words recalled across different steps of an exemplary embodiment of a RAVLT test is provided in FIG. 8. As shown in FIG. 8, the RAVLT test may include a plurality of different trials that are part of a learning phase 802 of the RAVLT trial (e.g., Trials I-V 811-815). In step 202, the computing device 110 may retrieve speech data that are part of this learning phase 802 of the RAVLT trial as the training baseline speech data 112. FIG. 8 also shows that the RAVLT test includes different types of recall trials: Distraction trial B 822, Post-distraction recall 824, and 20-minute delayed recall 826. The computing device 110 may retrieve speech data collected during any one of these recall trials as training trial speech data 114 for step 202.

In step 204, the computing device 110 analyzes and extracts a plurality of speech features from each of the sets of speech data received from the database 110: (i) the plurality of sets of training baseline speech data 112, and (ii) the set of training trial speech data 114. In particular, the computing device 110 extracts a set of the same types of speech features from each of the above data sets. The computing device 110 may extract as speech features from the sets of speech data any suitable type of acoustics properties for analyzing audio recordings of spoken speech, including mean and standard deviation data values corresponding to such acoustic properties. For example, the speech features may include one or more of the exemplary acoustic properties of audio recordings of speech listed and defined below in Table 1. In some embodiments, the speech features may include all or a subset of mean and/or standard deviation data values corresponding to these exemplary acoustic properties across frames of audio recordings of speech.

TABLE 1

| Acoustic Properties | Definition |
| --- | --- |
| Pitch | Frequency of the first harmonic |
| Amp_ratio_1000_Hz | $\dfrac{\text{Amplitude contained in 0--1000 Hz}}{\text{Amplitude contained in 0--4000 Hz}}$ |
| Amp_ratio_400_Hz | $\dfrac{\text{Amplitude contained in 0--400 Hz}}{\text{Amplitude contained in 0--4000 Hz}}$ |
| Chirp | Derivative of the pitch (tracks how fast pitch is changing) |
| Fractional Chirp (Normalized Chirp) | $\dfrac{\text{Chirp}}{\text{Pitch}}$ (higher pitches have higher chirps) |
| Mel Frequency | Mel-Frequency amplitude |
| MFCC | Mel-Frequency Cepstral Coefficients (spectral content) |
| Energy | Energy of spectrogram |
| Low frequency energy | Low frequency energy (in the 250-650 Hz frequency band) |
| High frequency energy | High frequency energy (in the 1000-4000 Hz frequency band) |
| Pauses | Duration of pause segments (in seconds) |
| Voices | Duration of voice segments (in seconds) |

The computing device 120 may extract from each speech data set any suitable number of speech features. An increased number of speech features may improve predictive and/or analytical performance of the systems and methods of the present application but may become computationally burdensome. Therefore, an appropriate number of speech features may be selected to balance predictive and/or analytical performance with computational efficiency. In some embodiments, the computing device 120 may extract from each speech data set at least 24, at least 30, at least 50 or at least 100 different speech features. In one embodiment, the computing device 120 may extract from each speech data set from 5 to 150 speech features, from 10 to 100 speech features, from 12 to 50 speech features.

Figure 3:
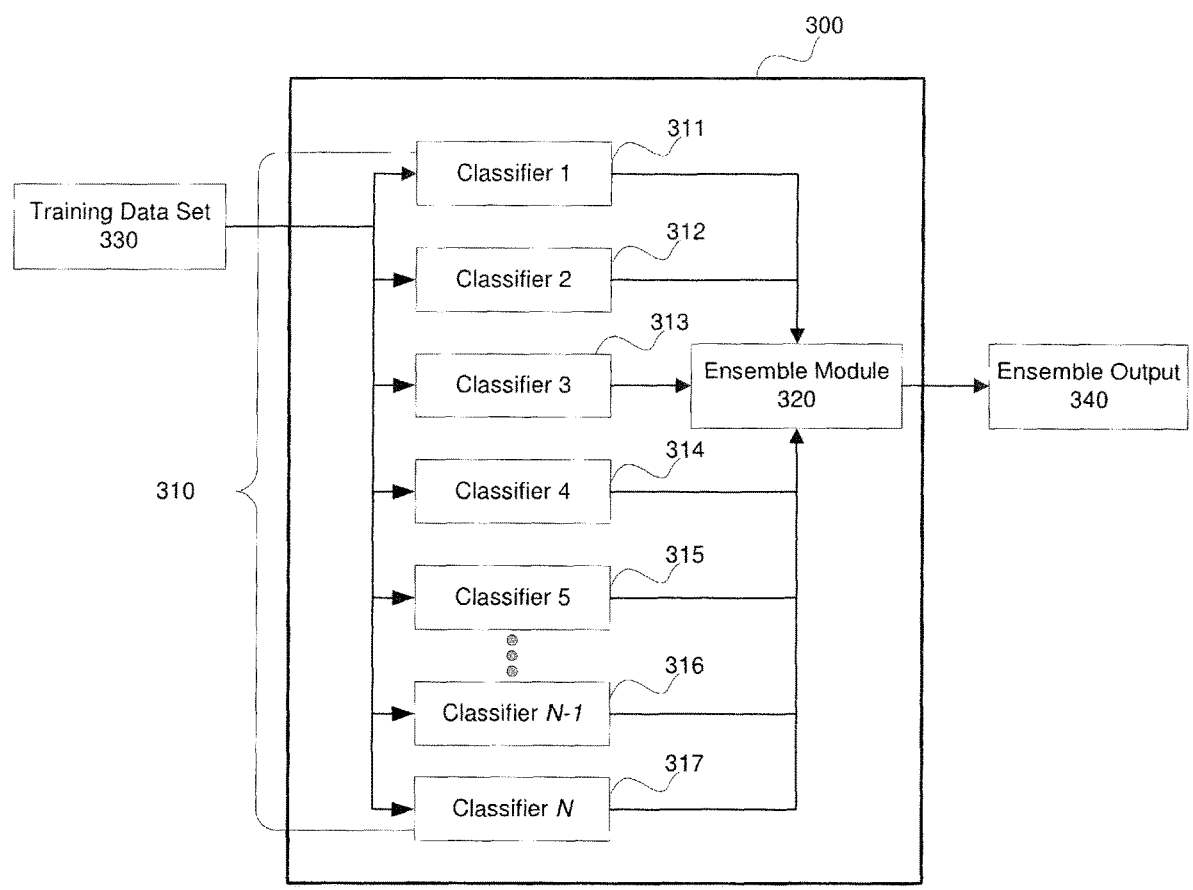
FIG. 3 shows an ensemble classifier comprising a plurality of component classifiers and an ensemble module, according to an exemplary embodiment of the present application.

In step 206, the computing device 120 generates an ensemble classifier 300 based on the set of training trial speech data 114 received from the database 110 and the associated speech features for the training trial speech data 114 obtained in the previous step (step 204). As shown in FIG. 3, the ensemble classifier 300 comprises a plurality of component classifiers 310, and an ensemble module 320. Each of the component classifiers 310 is a machine-learning classifier configured to generate a component output identifying a sample data as corresponding to that of a normal patient or a cognitive decline patient. When the component classifiers 310 are trained using data obtained from normal and MCI patients, the component classifiers 310 are each machine-learning classifiers configured to generate a component output identifying the sample data as corresponding to that or a normal patient or a MCI patient. More particularly, each of the component classifiers 310 is a support vector machine (SVM). It is also contemplated that each of the component classifiers 310 may alternatively utilize other suitable supervised learning modules, such as, for example, a logistic regression module, an Extreme Gradient Boosting module, a Random Forest module or a Naive Bayes module.

Each of the component classifiers 310 is generated by the computing device 120 to analyze a down-sampled subset of the speech features of the training trial speech data 114. For each component classifier 310, the subset of speech features is independently selected using the method 400 shown in FIG. 4 and described further below. The ensemble classifier 300 may include any suitable number, N, of component classifiers 310. For example, the ensemble classifier 300 may include at least 10, at least 20, at least 30 or at least 50 component classifiers 310. In one specific embodiment, the ensemble classifier 300 includes 30 component classifiers 310.

The ensemble module 320 is configured to receive the component outputs from all of the component classifiers 310 and generate an ensemble output 340 identifying the sample data as corresponding to the normal patient or the MCI patient based on the component outputs. The ensemble module 320 may utilize any suitable method for determining the ensemble output 340 based on the component outputs provided by each of the component classifiers 310. For example, the ensemble module 320 may utilize a bagging or aggregating method that receives and considers the component outputs from each of the component classifiers 310 with equal weight. Alternatively, the ensemble module 320 may utilize other methods where the component outputs are weighted differently, e.g., an adaptive boosting method, or a gradient boosting method.

Figure 4:
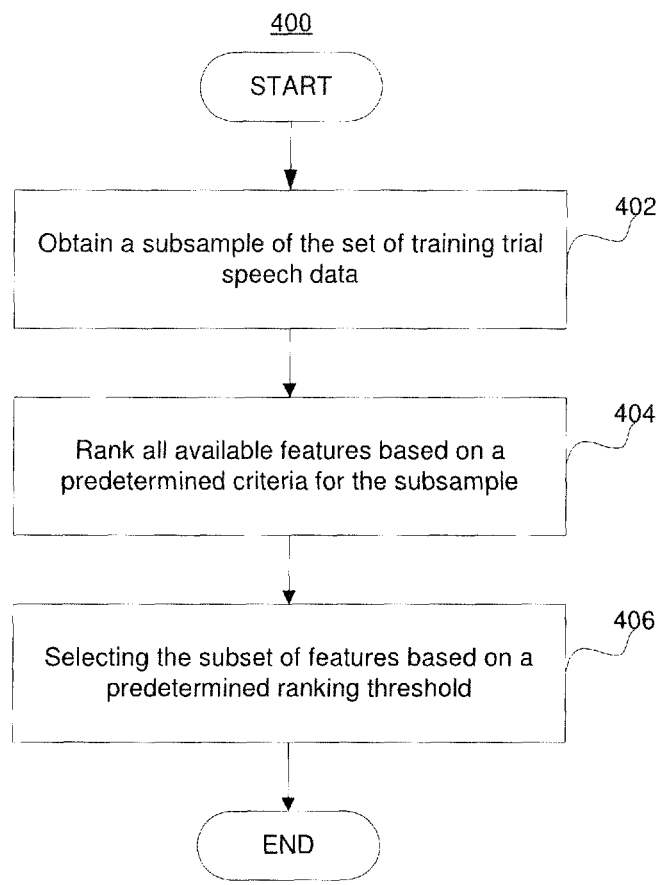
FIG. 4 shows a method for independently selecting a subset of the speech features for each component classifier of the exemplary ensemble classifier of FIG. 3.

FIG. 4 shows an exemplary embodiment of a method 400 for independently selecting a subset of the speech features for each component classifier 310. The computing device 120 repeats the method 400 each time step 206 selects a desired down-sampled subset of speech features for generating each component classifier 310. In other words, the computing device 120 analyzes the training trial speech data 114 using method 400 to select a desired down-sampled subset of speech features for generating a first component classifier 311, repeats the analysis to selected a different down-sampled subset of speech features to generate a next component classifier 312, and further repeats the analysis to generate subsequent component classifiers 313-317 until the computing device 120 has selected a down-sampled subset of speech features and generated the N-th component classifier 317. The method 400 selects a different down-sampled subset of speech features for each of the component classifiers 310, which allows the computing device 120 to generate an ensemble classifier 300 having component classifiers 310 that each model only a subset of all available speech features, but collectively sample across a greater number of speech features. This structure of the ensemble classifier 300 provides a module having improved predictive and/or analytic performance that incorporates a greater number of speech features while limiting each of the component classifiers 310 to analyze only the selected subset of speech features for each component classifier to provided improved computational efficiency.

In step 402, the computing device 120 analyzes the training trial speech data 114 to obtain a subsample of the training trial speech data 114. As discussed below, this subsample is used by the computing device 120 to identify desired parameters and features for a component classifier 310 generated for a reduced number of speech features. The subsample includes a first number of samples of the training trial speech data 114 that are from normal patients and a second number of samples of the training trial speech data 114 that are from cognitive decline patients. The first number of samples may be randomly selected from entries in the training trial speech data 114 that are from normal patients.

Similarly, the second number of samples may be randomly selected from entries in the training trial speech data 114 that are from cognitive decline patients. To provide substantial balance between the two different classes of patients (i.e., normal patients and cognitive decline patients) in step 402, the second number of samples is at least 80% of the first number of samples, at least 90% of the first number of samples, or at least 95% of the first number of samples. Preferably, the subsample is balanced so that a ratio of the first number of samples to the second number of samples is 1:1. This preferred subsampling allows the remainder of method 400 to proceed with data that is equally balanced between the two classes: normal patients and cognitive decline patients. Typically, the training trial speech data 114 can include a larger number of normal patients than cognitive decline patients and therefore, provide data that is imbalanced between the two classes. The balanced subsampling helps to address any class imbalance that may be in the training trial speech data 114 that would otherwise lead to a classifier that is biased towards the larger class—the normal patients—which can lead to false negatives in the classifier and miss patients who should otherwise be identified as corresponding to cognitive decline patients. Therefore, the ensemble classifier 300 combines several individual component classifiers 310 for subsets of speech features that are selected using substantially equal or equal proportion of normal and cognitive decline patients and therefore, provides a classifier that is balanced, samples across different speech features, and is, therefore, capable of learning from the entirety of the training data set.

In step 404, the computing device 120 analyzes all of the speech features of the subsample of the training trial speech data 114 and ranks the speech features based on a predetermined criteria. The speech features may be ranked based on any suitable statistical criteria for identifying those features that contribute most significantly to feature discriminatory signals as observed in the subsample of the training trial speech data 114. In particular, the speech features may be ranked based on the feature importance of each of the speech features to the subsample of the training trial speech data 114. Specifically, when the component classifier 310 is a SVM, the computing device 120 may rank the speech features based on their importance in specifying the difference (e.g., decision boundary) between normal and cognitive decline patients as observed in the subsample obtained from the previous step (step 402). More specifically, each speech feature may be ranked by its corresponding coefficient to the SVM hyper plane (e.g., decision boundary) based on the subsample of the training trial speech data 114. Speech features having lower coefficients to the SVM hyper plane are considered relatively less significant to specifying the decision boundary of the SVM and are therefore, of lower feature importance and lower rank.

In step 406, the computing device 120 selects the subset of speech features based on a predetermined ranking threshold (e.g., selecting for only the top x speech features) from the ranking of speech features generated by the previous step (step 404). The selected subset of x speech features is used by the computing device 120 to generate a component classifier 310 for analyzing down-sampled x number of features. By selected the top x ranked speech features, the computing device 120 generates a component classifier 310 that models those features that most significantly contribute to the feature discriminatory signal contained within the training trial speech data 114 while limiting the computational cost of the component classifier 310 to the down-sampled number of x speech features. It is contemplated that any suitable number, x, of the top ranked features may be selected. For example, step 406 may select at least 10, at least 20, at least 30 of the top ranked features. In one specific embodiment, the top 20 ranked features are selected for each component classifier 310.

Returning to method 200, in step 208, the computing device 120 generates a training data set 330 for training the ensemble classifier 300 generated from the previous step (step 206). In particular, the computing device 120 generates a training data set 330 comprising the training trial speech data 114 normalized with the training baseline speech data 112, in particular, the plurality of sets of training baseline speech data 112. In one embodiment, the training baseline data 112 includes learning phase data from a WLR test (e.g., RAVLT test) and the training data set 330 is generated by normalizing the training trial speech data 114 with the learning phase data from the WLR tests. The resulting training data set from this embodiment provides quantitative values corresponding to cognitive loads of the group of normal and cognitive decline patients. Specifically, the computing device 120 generates a training data set 330 comprising each of the features of the training trial speech data 114 normalized with a mean of the corresponding feature across the plurality of sets of training baseline speech data 112. More specifically, each feature of the training data set 330 may be obtained by subtracting the mean value of the feature across the plurality of sets of training baseline speech data 112 from the feature of the training trial speech data 114. Normalization of the speech features of the training trial speech data 114 with the plurality of sets of training baseline speech data 112 may enhance the feature discriminatory signals contained within the training trial speech data 114 and improve the predictive and/or analytic performance of an ensemble classifier 300 trained with such normalized data.

In step 210, the computing device 120 trains the ensemble classifier 300 using the training data set 330 generated by step 208 to generate a trained ensemble classifier 516. Each of the component classifiers 310 are trained with a down-sampled portion of the training data set 330 corresponding to the subset of features selected to be modeled by the component classifier. Therefore, a unique down-sampled portion of the training data set 330 is provided to train each of the component classifiers 310. In other words, the down-sampled portion of the training data set 330 for training component classifier 311 is different from the down-sampled portion of the training data set 330 for training the other component classifiers 312-317. The trained ensemble classifier 516 comprises component classifiers 310 each having selected a subset of speech features along with corresponding weighted coefficient values for each feature generated from training the component classifiers 310 with the training data set 330. The trained ensemble classifier 516 may be stored in any suitable memory and may be loaded to user devices for analyzing new patient speech data to detect and/or predict cognitive decline, in particular, MCI, in a subject.

Figure 5:
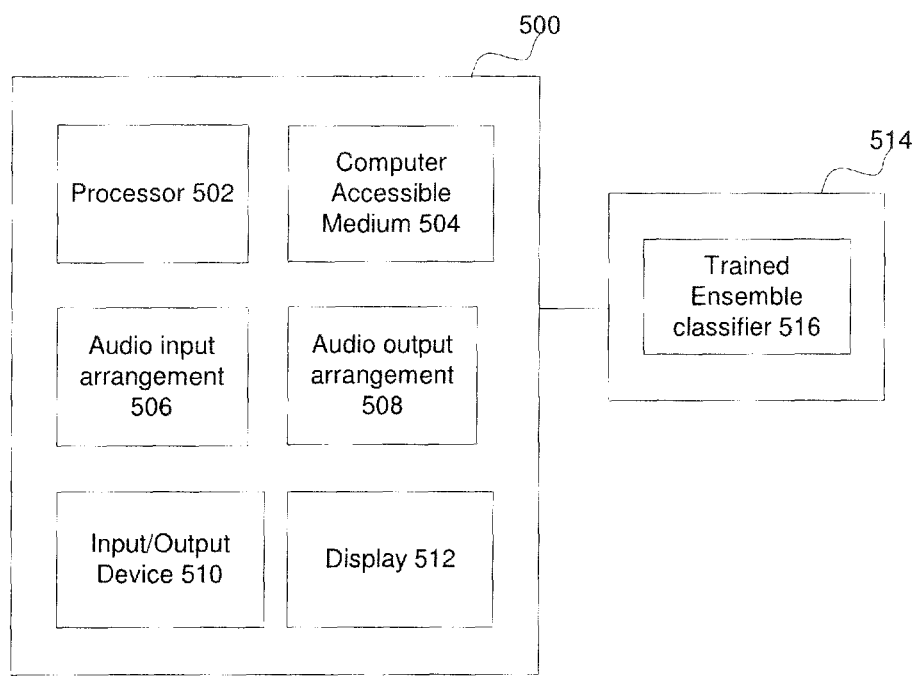
FIG. 5 shows a device for detecting cognitive decline based on a speech sample of a subject, according to an exemplary embodiment of the present application.

FIG. 5 shows an exemplary device 500 for detecting and/or predicting cognitive decline in a subject based on a speech sample of the subject. The device 500 utilizes the trained ensemble classifier 516, as generated and trained by method 200 discussed above. The device 500 comprises an audio input arrangement 506 for receiving audio signals and generating data corresponding to recordings of the audio signals. For example, the audio input arrangement 506 may comprise a microphone for capturing vocalized speech of a subject. The device 500 may also comprise an audio output arrangement 508 for generating an audio output. For example, the audio output arrangement 508 may comprise a speaker for audibly providing instructions for a WLR test to a subject. The device 500 also comprises a display 512 for generating a visual output to a user. The device 500 may further comprise an input/output device 510 for receiving and/or transmitting data or instructions to or from the device 500. The device 500 further comprises a processor 502 and a computer accessible medium 504. The processor 502 is operably connected to the audio output arrangement 508 and the display 512 to control audio and visual output of the device 500. The processor 502 is also operably connected to the audio input arrangement 506 to receive and analyze data corresponding to audio recordings captured by the audio input arrangement 506. The processor 502 can include, e.g., one or more microprocessors, and use instructions stored on the computer-accessible medium 504 (e.g., memory storage device). The computer-accessible medium 504 may, for example, be a non-transitory computer-accessible medium containing executable instructions therein. The device 500 may further include a memory storage device 514 provided separately from the computer accessible medium 504 for storing the trained ensemble classifier 516. The memory storage device 514 may be part of the device 500 or may be external to and operably connected to the device 500.

Figure 6:
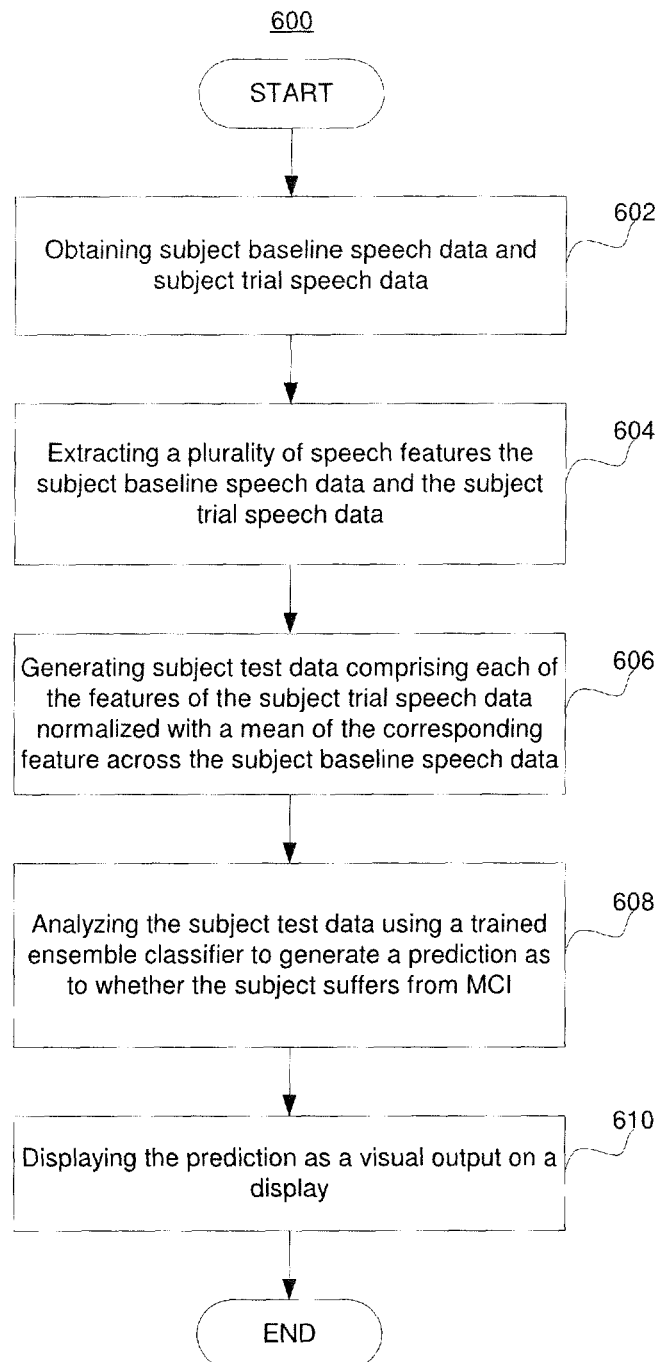
FIG. 6 shows a method for detecting cognitive decline based on a speech sample of a subject, according to an exemplary embodiment of the present application.

FIG. 6 shows an exemplary method 600 for detecting and/or predicting cognitive decline in a subject based on a speech sample of the subject, according an exemplary embodiment of the present application. In particular, the method 600 obtains a WLR speech sample from the subject to determine whether the sample correlates more to that of a normal or a cognitive decline patient. In step 602, the subject is provided with a first set of instructions a plurality of times by a clinician operating the device 500 or by the processor 502 directing the audio output arrangement 506 to audibly provide the first set of instructions to the patient, and the processor 502 receives from the audio input arrangement 506 subject baseline speech data corresponding to a plurality of audio recordings of speech of a subject in response to the first set of instructions. The subject is also provided with a second set of instructions by the clinician or by the processor 502 directing the audio output arrangement 506 to audibly provide the second set of instructions, and the processor 502 receives from the audio input arrangement 506 subject trial speech data corresponding to an audio recording of speech of a subject in response to the second set of instructions. The first set of instructions may correspond to those instructions used in step 202 discussed above for generating the training baseline speech data 112, and the second set of instructions may correspond to those instructions used in step 202 for generating the training trial speech data 114.

In step 604, the processor 502 analyzes and extracts a plurality of features from the subject baseline speech data and the subject trial speech data in a similar manner as discussed above with respect to step 204. In step 606, the processor 502 generates subject test data comprising each of the features of the subject trial speech data normalized with the corresponding feature of the subject baseline speech data in a similar manner as discussed above with respect to the training data set in step 208. Similar to step 208, the subject baseline speech data, in one embodiment, includes learning phase data from a WLR test (e.g., RAVLT test) administered to the subject, and the subject test data is generated by normalizing the subject trial speech data with the learning phase data from the WLR tests. The resulting subject test data from this embodiment provides quantitative values corresponding to the cognitive load of the subject. In step 608, the processor 502 analyzes the subject test data using the trained ensemble classifier 516. Each of the plurality of component classifiers 310 of the trained ensemble classifier 516 analyzes the subject test data to generate a component output identifying the subject test data as corresponding to a normal patient or a cognitive decline patient. The ensemble module 320 of the trained ensemble classifier 516 receives the component outputs from the component classifiers 310 and analyzes the component outputs to generate an ensemble output identifying the subject test data as corresponding to the normal patient or the cognitive decline patient. The processor 502 may also generate an output indicating whether the subject has an increased risk for neurodegeneration and/or likely suffers from cognitive decline based on the ensemble output generated by the trained ensemble classifier 516 from analyzing the subject test data. The output may indicate that the subject has an increased risk for neurodegeneration and/or likely suffers from cognitive decline when the ensemble output identifies the subject test data as corresponding to the cognitive decline patient. In contrast, the output may indicate that the subject does not have an increased risk for neurodegeneration and/or is not likely to suffer from cognitive decline when the ensemble output identifies the subject test data as corresponding to the normal patient. In step 610, the processor 502 directs the display 512 to provide a visual display showing the output.

The ensemble output generated by the trained ensemble classifier 516 from analyzing the subject test data and/or the output generated by the device 500 may be provide to a clinician to screen and identify those patients that have an increased risk for neurodegeneration and/or suffer from cognitive decline, including but not limited to decline in verbal episodic memory, decreased rate of learning, decline in short-term verbal memory, decline in delayed verbal memory, decline in recall performance after interference stimulus, decline in recognition memory, etc. Subject whose subject test data are identified by the ensemble output as corresponding to a cognitive decline patient may be at an increased risk for developing neurodegenerative disorders, such as, AD or another type of dementia. Therefore, the ensemble output generated from analyzing the subject test data and/or the output generated by the device 500 may assist a clinician in directing at-risk patients to further cognitive tests so as to confirm the ensemble output and/or output from method 600. Thus, device and method of the present application allows for earlier identification of those patients at risk of neurodegeneration and provide better care for these at-risk patients, and/or to initiate treatment at an earlier stage of cognitive decline than conventional diagnosis of neurodegenerative disorders, dementia, or AD. Furthermore, when the ensemble output indicates that the subject test data corresponds to a cognitive decline patient and/or the output generated by the device 500 indicates that the subject has an increased risk for neurodegeneration and/or is likely to suffer from cognitive decline, the processor 502 generate instructions for administration of a treatment to the subject. In some embodiments, the instructions may direct administration of the treatment automatically, without any intervening user intervention.

Suitable treatments may include treatments for improving cognitive capacity and/or treatments for ameliorating deterioration of cognitive capacity. In one example, the treatment may comprise non-pharmacological treatments, such as, for example, digital therapeutics (e.g., a brain training module) to improve cognitive capacity of the subject. In some embodiments, the digital therapeutics may be automatically initiated when the ensemble output indicates that the subject test data corresponds to a cognitive decline patient and/or the output generated by the device 500 indicates that the subject has an increased risk for neurodegeneration and/or is likely to suffer from cognitive decline. The brain training module comprises a set of instructions executable by the processor for administer brain training exercises to improve cognitive capacity of the subject. The brain training module may be connected to a user interface to display braining training exercise instructions to the subject and receive input from the user in response to such instructions.

In another example, the treatments may comprise administration of one or more pharmaceutically active agents for preventing and/or ameliorating progression of neurodegeneration. In particular, the treatments may comprise administration of one or more pharmaceutically active agents for one or more pharmaceutically active agents for preventing and/or ameliorating progression of dementia, or more specifically for preventing and/or ameliorating progression of AD. Suitable pharmaceutically active agents may include one or more pharmaceutical active agents for preventing or reducing aggregation of beta-amyloid protein or tau protein in the brain, improving synaptic or cellular resilience of the brain, modulating expression of ApoE4 gene, modulating neuroinflammation related pathways, etc. In one example, the pharmaceutically active agents may comprise antipsychotics, acetylcholinesterase inhibitors, etc.

Those skilled in the art will understand that the exemplary embodiments described herein may be implemented in any number of manners, including as a separate software module, as a combination of hardware and software, etc. For example, the exemplary methods may be embodiment in one or more programs stored in a non-transitory storage medium and containing lines of code that, when compiled, may be executed by one or more processor cores or a separate processor. A system according to one embodiment comprises a plurality of processor cores and a set of instructions executing on the plurality of processor cores to perform the exemplary methods discussed above. The processor cores or separate processor may be incorporated in or may communicate with any suitable electronic device, for example, on board processing arrangements within the device or processing arrangements external to the device, e.g., a mobile computing device, a smart phone, a computing tablet, a computing device, etc., that may be in communications with at least a portion of the device.

EXAMPLE

Example I

In Example I, an exemplary word list recall test was administered manually by an examiner (similar to that of the RAVLT test) and also administered via a computer device to a total of 106 patients, of which 84 were normal and 22 suffered from MCI. Each of the patients was provided with a first set of instructions for listening to a first word list and immediately recalling and speaking the first word list. The first word list includes the following words: drum, helmet, music, coffee, school, parent, machine, garden, radio, farmer, nose, sailor, color, house, river. The speech was recorded for each patient to generate a set of baseline speech data corresponding to the speech recordings. The presentation of the first word list and immediate recall was repeated for the entire group of patients for a total of 5 times to generate 5 different sets of baseline speech data.

The patients were then subject to a distraction task. In particular, each of the patients was subsequently provided with a second set of instructions for listening to a second word list and recalling and speaking the second word list. The second word list includes the following words: desk, ranger, bird, shoe, stove, mountain, glasses, towel, cloud, boat, lamb, bell, pencil, church, fish. The speech was recorded for each patient to generate a set of trial speech data corresponding to the speech recordings for a Distractor Trial. After the distraction task, the patients were then asked to recall and speak the first word list. The speech was recorded for each patient to generate a set of trial speech data corresponding to the speech recordings for a Post Distraction Trial. After a 20-minute delay, the patients were then asked again to recall and speak the first word list. The speech was recorded for each patient to generate a set of trial speech data corresponding to the speech recordings for a Delayed Recall Trial.

Figure 7:
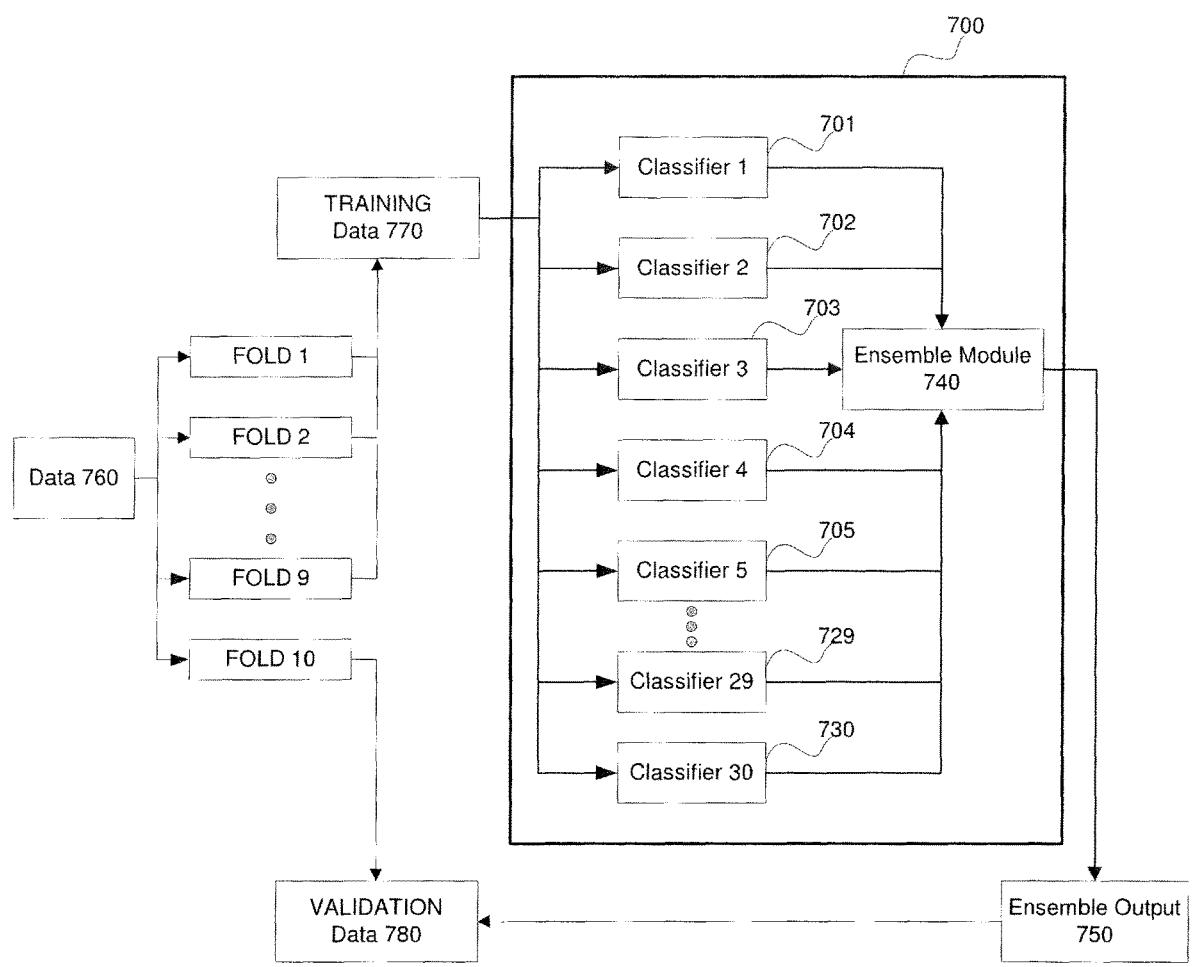
FIG. 7 shows an exemplary system comprising an ensemble classifier for detecting cognitive decline based on a speech sample of a subject, according to Example I of the present application

An exemplary set of speech features, e.g., mean and standard deviation values for the exemplary acoustic properties (as listed above in Table 1) across speech frames of audio recordings of speech, were extracted from each of the 5 different sets of baseline speech data, the set of trial speech data for the Distractor Trial, the set of trial speech data for the Post-Distraction Trial, and the set of trial speech data for the Delayed Recall Trial. The exemplary ensemble classifier 700 of Example I is shown in FIG. 7. The ensemble classifier 700 includes component classifiers 701-730 and an ensemble module 740 receiving component outputs from the component classifiers 701-730 and generate an ensemble output 750. As shown in FIG. 7, the ensemble classifier 700 of Example I comprises 30 component classifiers 701-730 each being a support vector machine (SVM) generated based on a down-sampled subset of top 20 features determined based on a subsample of training data balanced between those correlated to control patients and those correlated to MCI patients. Specifically, the subsample includes 20 entries corresponding to control patients and 20 entries corresponding to MCI patients.

As shown in FIG. 7, the ensemble classifier 700 is trained and validated by 10-fold cross-validation using a set of data 760 comprising each of the features of trial speech data normalized with a mean of the corresponding feature across the 5 sets of baseline speech data. As shown in FIG. 7, the data 760 is randomly distributed and partitioned into 10 folds of equal sizes. Of these 10-fold partitions, data from 9 of the folds are used as training data 770 for the ensemble classifier 700 with the remaining fold being used as validation data 780. Training and validation are repeated using a different fold as the validation data 780 while the remaining folds are used as training data 770 until each fold has been used once as validation data 780. Although Example I utilizes a 10-fold cross-validation method. It is contemplated that the ensemble classifier 700 may be validated using a k-fold cross-validation method, wherein k is any suitable positive integer.

The mean values for certain performance measures generated based on the validation data across each of the 10-folds for each of the Distractor Trial, Post-Distractor Trial, and Delayed Recall Trial is provided below in Table 2. As shown in the performance measures of Table 2, the Post-Distraction Trial has the highest discriminatory signal between MCI and normal patients, which is followed by the Distractor Trial and then the Delayed Recall Trial.

TABLE 2

| Performance Measures | Distractor Trial | Post-Distraction Trial | Delayed Recall Trial |
|---|---|---|---|
| Accuracy | 0.65 | 0.66 | 0.61 |
| Sensitivity | 0.57 | 0.75 | 0.70 |
| Specificity | 0.67 | 0.64 | 0.59 |
| Balanced Accuracy | 0.62 | 0.69 | 0.65 |
| Positive Predictive Value | 0.31 | 0.35 | 0.31 |
| Negative Predictive Value | 0.86 | 0.91 | 0.88 |
| DOR | 2.70 | 5.26 | 3.42 |
| F-measure | 0.40 | 0.48 | 0.43 |
| Mean value of Area Under the Curve (AUC) for Receiver Operating Characteristics (ROC) curve | 0.68 | 0.73 | 0.65 |
| Standard Deviation of AUC for ROC | 0.16 | 0.12 | 0.18 |

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method for predicting cognitive decline in a subject comprising:
    obtaining subject baseline speech data corresponding to a plurality of audio recordings of speech of the subject in response to a first set of instructions provided to the subject;
    obtaining subject trial speech data corresponding to a further audio recording of speech of the subject in response to a second set of instructions provided to the subject;
    extracting a plurality of features from the subject baseline speech data and the subject trial speech data;
    generating subject test data by normalizing the subject trial speech data using the subject baseline speech data; and
    analyzing the subject test data using a trained ensemble classifier, the trained ensemble classifier comprising:
        a plurality of component classifiers and an ensemble module, wherein
            each of the plurality of component classifiers is configured to generate a component output identifying the subject test data as corresponding to a normal patient or a cognitive decline patient, each component classifier configured to analyze a subset of features selected from the plurality of features, and
            the ensemble module is configured to receive the component outputs from the component classifiers and generate an ensemble output identifying the subject test data as corresponding to the normal patient or the cognitive decline patient based on the component outputs,
        wherein the plurality of component classifiers is trained using training baseline speech data corresponding to prior audio recordings of speech of a group of normal and cognitive decline patients in response to the first set of instructions, and training trial speech data corresponds to prior audio recordings of speech of the group normal and cognitive decline patients in response to the second set of instructions;
    wherein the subset of features of the trained ensemble classifier is independently selected during training for each of the plurality of component classifiers by the steps comprising:
        ranking the plurality of features for a subsample of the training trial speech data based on feature importance, the subsample consisting of a first number of samples of the training trial speech data corresponding to normal patients and a second number of samples of the training trial speech data corresponding to cognitive decline patients, and
        selecting the subset of features from the plurality of features based on a predetermined ranking threshold.

2. The method of claim 1, wherein the plurality of component classifiers is trained using a training data set generated by normalizing training trial speech data using training baseline speech data.

3. The method of claim 1, wherein the method predicts Mild Cognitive Impairment (MCI) in the subject, and the group of normal and cognitive decline patients consists of normal and MCI patients.

4. The method of claim 1, wherein each of the plurality of component classifiers comprises a plurality of weighted feature coefficients trained using the training baseline speech data and the training trial speech data.

5. The method of claim 1, further comprising:
    displaying an output indicating the subject likely suffers from cognitive decline when the ensemble output identifies the subject test data as corresponding to the cognitive decline patient, and an output indicating the subject is not likely to suffer from cognitive decline when the ensemble output identifies the subject test data as corresponding to the normal patient.

6. The method of claim 1, further comprising:
    administering a treatment for improving cognitive capacity or for ameliorating deterioration of cognitive capacity when the ensemble output identifies the subject test data as corresponding to the cognitive decline patient.

7. The method of claim 1, further comprising:
    administering a pharmaceutically active agent for preventing or ameliorating progression of dementia when the ensemble output identifies the subject test data as corresponding to the cognitive decline patient.

8. The method of claim 1, further comprising:
    administering for a pharmaceutically active agent for preventing or reducing aggregation of beta-amyloid protein or tau protein in a brain of the subject when the ensemble output identifies the subject test data as corresponding to the cognitive decline patient.

9. The method of claim 1, wherein the second number of samples is at least 80% of the first number of samples.

10. The method of claim 9, wherein a ratio of the first number of samples to the second number of samples is 1:1.

11. The method of claim 1, wherein each of the plurality of component classifiers is a machine-learning classifier.

12. The method of claim 11, wherein each of the plurality of component classifiers is a support vector machine (SVM).

13. The method of claim 1, further comprising:
    generating an output indicating the subject has a decline in verbal episodic memory based on the ensemble output when the ensemble output identifies the subject test data as corresponding to the cognitive decline patient.

14. The method of claim 13, wherein the first set of instructions correspond to a word list recall test, and the second set of instructions correspond to a time-delayed word list recall test.

15. A computer-implemented method for training a classification system, the classification system configured to predict cognitive decline in a subject based on a speech sample of the subject, the method comprising:
obtaining training baseline speech data and training trial speech data from a group of normal and cognitive decline patients, the training baseline speech data corresponding to audio recordings of speech of the group of normal and cognitive decline patients in response to a first set of instructions and the training trial speech data corresponding to audio recordings of speech of the group of normal and cognitive decline patients in response to a second set of instructions;
extracting a plurality of features from (i) the training baseline speech data, and (ii) the training trial speech data;
generating an ensemble classifier comprising a plurality of component classifiers and an ensemble module, wherein
each of the plurality of component classifiers is configured to generate a component output identifying a sample data as corresponding to a normal patient or a cognitive decline patient, each component classifier configured to analyze a subset of features selected from the plurality of features,
the ensemble module is configured to receive the component outputs from the component classifiers and generate an ensemble output identifying the sample data as corresponding to the normal patient or the cognitive decline patient based on the component outputs,
the subset of features is independently selected from the plurality of features for each of the plurality of component classifiers by the steps comprising:
ranking the plurality of features for a subsample of the training trial speech data based on feature importance, the subsample consisting of a first number of samples of the training trial speech data corresponding to normal patients and a second number of samples of training trial speech data corresponding to cognitive decline patients, and
selecting the subset of features from the plurality of features based on a predetermined ranking threshold;
generating a training data set by normalizing the training trial speech data using the training baseline speech data; and
training the ensemble classifier using the training data set.

16. A system for training a classification system, the classification system configured to predict cognitive decline in a subject based on a speech sample of the subject, the system comprising:
a database configured to store training baseline speech data and training trial speech data from a group of normal and cognitive decline patients, the training baseline speech data corresponding to audio recordings of speech of the group of normal and cognitive decline patients in response to a first set of instructions and the training trial speech data corresponding to audio recordings of speech of the group of normal and cognitive decline patients in response to a second set of instructions;
a computing device operably connected to communicate with the database, the computing device comprising a processor and a non-transitory computer readable storage medium including a set of instructions executable by the processor, the set of instructions operable to:
retrieve the training baseline speech data and the training trial speech data from the database,
extract a plurality of features from (i) the training baseline speech data, and (ii) the training trial speech data,
generate an ensemble classifier comprising a plurality of component classifiers and an ensemble module, wherein
each of the plurality of component classifiers is configured to generate a component output identifying a sample data as corresponding to a normal patient or a cognitive decline patient, each component classifier configured to analyze a subset of features selected from the plurality of features, and
the ensemble module is configured to receive the component outputs from the component classifiers and generate an ensemble output identifying the sample data as corresponding to the normal patient or the cognitive decline patient based on the component outputs,
independently select the subset of features for each of the plurality of component classifiers from the plurality of features by the steps comprising:
ranking the plurality of features for a subsample of the training trial speech data based on feature importance, the subsample consisting of a first number of samples of the training trial speech data corresponding to normal patients and a second number of samples of training trial speech data corresponding to cognitive decline patients, and
selecting the subset of features from the plurality of features based on a predetermined ranking threshold,
generate a training data set by normalizing the training trial speech data using the training baseline speech data, and
train the ensemble classifier using the training data set; and
a memory configured to store the trained ensemble classifier.

* * * * *